US008262582B2

(12) United States Patent
Kortelainen

(10) Patent No.: US 8,262,582 B2
(45) Date of Patent: Sep. 11, 2012

(54) EXTRACTION OF HEART INTER BEAT INTERVAL FROM MULTICHANNEL MEASUREMENTS

(75) Inventor: Juha M. Kortelainen, Tampere (FI)

(73) Assignee: Valtion Teknillinen Tutkimuskeskus, VTT (FI)

( * ) Notice: Subject to any disclaimer, the term of this patent is extended or adjusted under 35 U.S.C. 154(b) by 503 days.

(21) Appl. No.: 12/544,630

(22) Filed: Aug. 20, 2009

(65) Prior Publication Data

US 2010/0249628 A1 Sep. 30, 2010

Related U.S. Application Data

(60) Provisional application No. 61/091,146, filed on Aug. 22, 2008.

(51) Int. Cl.
*A61B 5/02* (2006.01)
(52) U.S. Cl. .................................................. 600/527
(58) Field of Classification Search .................. 600/527
See application file for complete search history.

(56) References Cited

U.S. PATENT DOCUMENTS

| 4,679,569 A * | 7/1987 | Lee .................................. 600/527 |
| 2010/0016685 A1 * | 1/2010 | Muehlsteff et al. ............ 600/301 |

OTHER PUBLICATIONS

J. M. Kortelainen and J. Virkkala, "FFT averaging of multichannel BCG signals from bed mattress sensor to improve estimation of heart beat interval," in Proc. IEEE Eng. Med. Biol. Soc. 29th Ann. Int. Conf., Cité Internationale, Lyon, France, 2007, pp. 6685-6688.*
S. Junnila, A. Akhbardeh, A. Värri, and T. Koivistoinen, "An EMFi-film sensor based ballistocardiographic chair: Performance and cycle extraction method," in Proc. IEEE Workshop Signal Process. Syst. Design Implementation, 2005, pp. 373-377.*
Alihanka, J., et al., *A New Method for Long-Term Monitoring of the Ballistocardiogram, Heart Rate, and Respiration*, American Physiological Society, 1981, R384-R392.

* cited by examiner

*Primary Examiner* — Carl H. Layno
*Assistant Examiner* — Tammie K Heller
(74) *Attorney, Agent, or Firm* — Alston & Bird LLP

(57) ABSTRACT

A monitoring apparatus comprising a multichannel pressure sensing sensor for measuring a ballistocardiographic signal of a human body is provided. The monitoring apparatus comprises a manner for selecting a time window for heart inter beat interval including two consecutive heart beats to be estimated, defining a spectrum for the signal averaging between at least two measurement channels of the sensor, a cepstrum from the logarithm of the spectrum, and a heart inter beat interval. A method for defining a heart inter beat interval is also provided, where a ballistocardiographic signal of a body is measured with a multichannel pressure sensing sensor, a time window for heart inter beat interval including two consecutive heart beats to be estimated is selected, a spectrum for the signal averaging between at least two measurement channels of the sensor, a cepstrum from the logarithm of the spectrum, and a heart inter beat interval are defined.

12 Claims, 5 Drawing Sheets

EXTRACTION OF HEART INTER BEAT INTERVAL FROM MULTICHANNEL MEASUREMENTS

CROSS REFERENCE TO RELATED APPLICATION

This application claims the benefit of U.S. Provisional Application No. 61/091,146, filed Aug. 22, 2008, the contents of which are incorporated herein in their entirety.

BACKGROUND OF THE INVENTION

1. Field of the Invention

The present invention relates to a monitoring apparatus for measuring ballistocardiographic signal (BCG) using a multichannel sensor intended to analyze this multichannel data with a cepstrum method for heart inter beat interval (heart IBI) and heart rate variability (HRV) calculation. The invention further relates to a method for analyzing this multichannel data with a cepstrum method for heart inter beat interval (heart IBI) and heart rate variability (HRV) calculation.

2. Background of the Invention

Heart rate variability (HRV) is the rate at which heartbeat changes in time. A HRV analysis gives markers for activity of the autonomic nervous system (ANS) and is applied, for example, for sleep/wakefulness monitoring, stress analyses and also to obtain information about the activity and condition of the heart. The standard HRV analysis is composed of different frequency ranges, and as an example the high frequency component HRV-HF in the range of 0.15 . . . 0.4 Hz shows the cardiopulmonary coupling as a coherence between heart rate and respiration cycle. The rhythm of a healthy heart under resting conditions is actually surprisingly irregular. These moment-to-moment variations in the heart rate are easily overlooked when average heart rate is calculated. Defining the HRV requires accurate measurement of the heart inter beat interval, which is usually the electrocardiogram RR interval (ECG RRI) measured using a contact electrode.

The results of ECG RRI measurement are accurate and have a good resolution, but at least standard devices of ECG measurement require direct contact to the patient's skin or body via cables or wires. This is uncomfortable in use e.g. during sleep and it means constraining the patient's movement to prevent disconnecting the sensors, and also creates a danger of entanglement or strangulation due to the cables. Additionally, these devices are complex to operate and require a trained individual to function properly. It is neither practical nor desirable to monitor people with bulky and obtrusive equipment There is a need to monitor people in their normal environment, for example at home in bed, when driving a car or at work. Heart IBI based on BCG signal, on the other hand, can be measured almost anywhere and it is an unobtrusive and non-invasive method, in which single channel pressure sensitive sensors in a bed mattress give feasible results for average heart rate per minute without the need for a trained individual, or the danger of entanglement or strangulation, but the accuracy and resolution is not adequate for HRV analyses, and analyses are not possible, which is obviously a problem.

Non-contact pressure sensors are largely used to measure BCG signal for detecting heart beat unobtrusively. The algorithms behind the existing commercial non-invasive single channel BCG bed mattress sensors have not been published, but they are probably based on filtering and pulse envelope triggering of single channel BCG. Usually, average heart rate is calculated by counting up the heart beat cycles during a longer time period e.g. one minute. Pulse envelope triggering is not accurate method when the BCG pulse shape varies strongly, causing variation that is not dependent on the actual heart beat interval, and causing error in comparison with the ECG RR-interval. The methods applied with Fourier Transform use long time windows for Discrete Fourier Transform (DFT), e.g. 20 seconds, to average the variance in time domain, which also decreases the time resolution and prevents detection of individual heart IBI value.

Sleep analyses can obviously be also improved by monitoring the respiration parameters. Sleep laboratories use additional sensors like the respiratory inductive plethysmogram (RIP) or the airflow methods for this purpose. When using a pressure sensor for the BCG recording, the respiration signal can be extracted as a low frequency component of the BCG signal.

One monitoring method is disclosed in the publication: J. Alihanka, K. Vaahtoranta and I. Saarikivi, "A new method for long-term monitoring of the ballistocardiogram, heart rate, and respiration", Am. J. Physiol. Regul. Integr. Comp. Physiol. 1981; vol. 240: 384-392, in which the principle of the static charge-sensitive-bed (SCSB) method is described. From the SCSB recording the BCG and respiratory movement can be recorded simultaneously by selective filtering of the original signal. The SCSB recording thus enables continuous long-term monitoring of the BCG, heart rate, respiratory rate, respiratory amplitude, and body movements e.g. during sleep. However, this method is not accurate enough for HRV analysis.

There exists a need for a multichannel sensor and a method for receiving more practicable non-contact BCG monitoring with better accuracy.

BRIEF SUMMARY OF THE INVENTION

The present invention is based on a multichannel pressure sensing sensor which may be integrated e.g. into a bed mattress, to collect BCG signal, and heart inter beat interval extracted from this multichannel BCG data with the cepstrum method, by applying Discrete Fourier Transform (DFT) for short time windows including at least one pair of consecutive heart beats. The invention further relates to a method for analyzing the BCG signal data from the multichannel pressure sensing sensor with the cepstrum method to receive heart inter beat interval to be used in HRV analysis.

One aim of the present invention is to analyze BCG signal measured using a multichannel pressure sensing sensor with the cepstrum method to receive heart inter beat interval with good resolution and accuracy in comparison with single channel BCG measurement of heart inter beat interval to be used in HRV analyzes.

The BCG is a vital sign in the 1 . . . 20 Hz frequency range which is caused by the mechanical movement of the heart and the pulsating blood flow and it can be recorded, for example, by a pressure sensing sensor from the pressing force of the body. BCG signal includes also respiratory movements, body movement artifacts and external vibration which make the detection of heart IBI more difficult.

In a preferred embodiment of the invention, the BCG sensor is in the form of a sheet, comprising a multichannel pressure sensing foil intended to be integrated into a bed mattress or a seat or wearable applications or the like. Sensor foils are applied to measure BCG unobtrusively e.g. while lying or sitting. There are a number of various suitable measuring arrangements for pressure sensitive foils, such as force sensing resistors (FSR), deformation of optical fibers, capacitive foils, piezoelectric polymer foil PVDF and electret foil Emfit. The multichannel pressure sensing sensor is usually a matrix-type, row-type or column-type multi-electrode multichannel pressure sensing sensor.

Preferably, the size for the sensor within the overall mattress area is sufficiently large and the number of electrodes is sufficient for collecting the required information concerning the heart movement and blood pulsation. However, it should be noticed that in some cases adequate accuracy could also be achieved with a smaller area and/or a smaller number of electrodes. In a preferred embodiment, the number of electrodes is about 8 channels and the size of multichannel sensor in bed mattress covers the area of about 1 meter in the length and 0.6 meter in the width. The shape of electrodes can be simply stripes in the width direction for a flat bed mattress or more optimized shape for integration into a seat. The number of measurement channels of the multichannel pressure sensing sensor corresponds to the number of electrodes. Sensor electrodes provide BCG signals from different locations under the body in the bed mattress. The characteristics of the BCG signal have strong variation even between adjacent measurement points. This variation has also a time-dependent behavior which is related, for example, to the respiration cycle and the sleep posture.

The sensor foil according to this invention could be placed inside or under a mattress made of rubber foam or other suitable material. The sensor foil can also be integrated into a seat to monitor the heart IBI and HRV of a seated person e.g. at home, at work or during travel.

The electronics used in the present invention is based on a multichannel signal converter, which can produce multiple digital signals representing a multiple of analogue signals. An example of this kind of a multichannel signal converter is a multichannel A/D converter. If an electret pressure sensor like Emfit foil is used, a charge amplifier is needed which can be designed most efficiently with a switched integrator amplifier, such as the commercial IC DDC118 from Texas Instruments. The main benefit is having a compact design for the multichannel A/D conversion of charge signals. Sensor data of channels is logged with adequate sampling rate, for example 50 Hz.

The cepstrum can be seen as information about the rate of change in the different spectrum bands. The cepstrum is commonly applied to extract time interval between consequent pulses in voiced or seismic echo signals. Cepstrum is close in definition with the autocorrelation function, which is also indexed by a lag time, with the difference that the inverse Fourier transform is taken from the squared spectrum i.e. power spectral density instead of the logarithm of the spectrum.

Fourier transform based cepstrum analyses of the BCG signal make it possible to calculate the time delay between two consecutive heart beat measurements, but the variance of pulse shape is high. However, the variance can be decreased by averaging between multichannel BCG signals. The heart beat interval varies strongly beat-to-beat, and thus the Fourier transform should only be done for each pair of consecutive heart beats. This adaptive time windowing is implemented in the algorithms based on filtering and pulse envelope triggering. The method can also be implemented with on-line calculation. Data processing with the cepstrum method can be processed e.g. with on-board DSP or with a PC processor after the data transfer.

According to a first aspect of the present invention there is provided a monitoring apparatus comprising:

a multichannel sensor for measuring a ballistocardiographic signal of a body, said multichannel sensor comprising at least two measurement channels;

a selector for selecting a time window for a heart inter beat interval including two consecutive heart beats to be estimated;

wherein the monitoring apparatus is configured for defining a spectrum for the ballistocardiographic signal for each selected time window;

forming an average of the ballistocardiographic signal spectra of at least two measurement channels of the multichannel sensor; and defining a heart inter beat interval on the basis of the averaged signal cepstrum.

According to a second aspect of the present invention there is provided a method for defining a heart inter beat interval comprising:

measuring a ballistocardiographic signal of a body with a multichannel sensor comprising at least two measurement channels;

selecting a time window for heart inter beat interval including two consecutive heart beats to be estimated;

defining a spectrum for the ballistocardiographic signal for each selected time window;

averaging between signal spectra of at least two measurement channels of the multichannel sensor; and defining a heart inter beat interval on the basis of the averaged signal cepstrum.

The method is a quite accurate and almost unnoticeable way to ensure the good quality of the BCG measurement to be used in the HRV calculation.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

In the following, the invention will be described with reference to the appended figures in which FIG. 1 shows a schema for a multichannel mattress foil sensor according to an embodiment of the invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Figure 1:
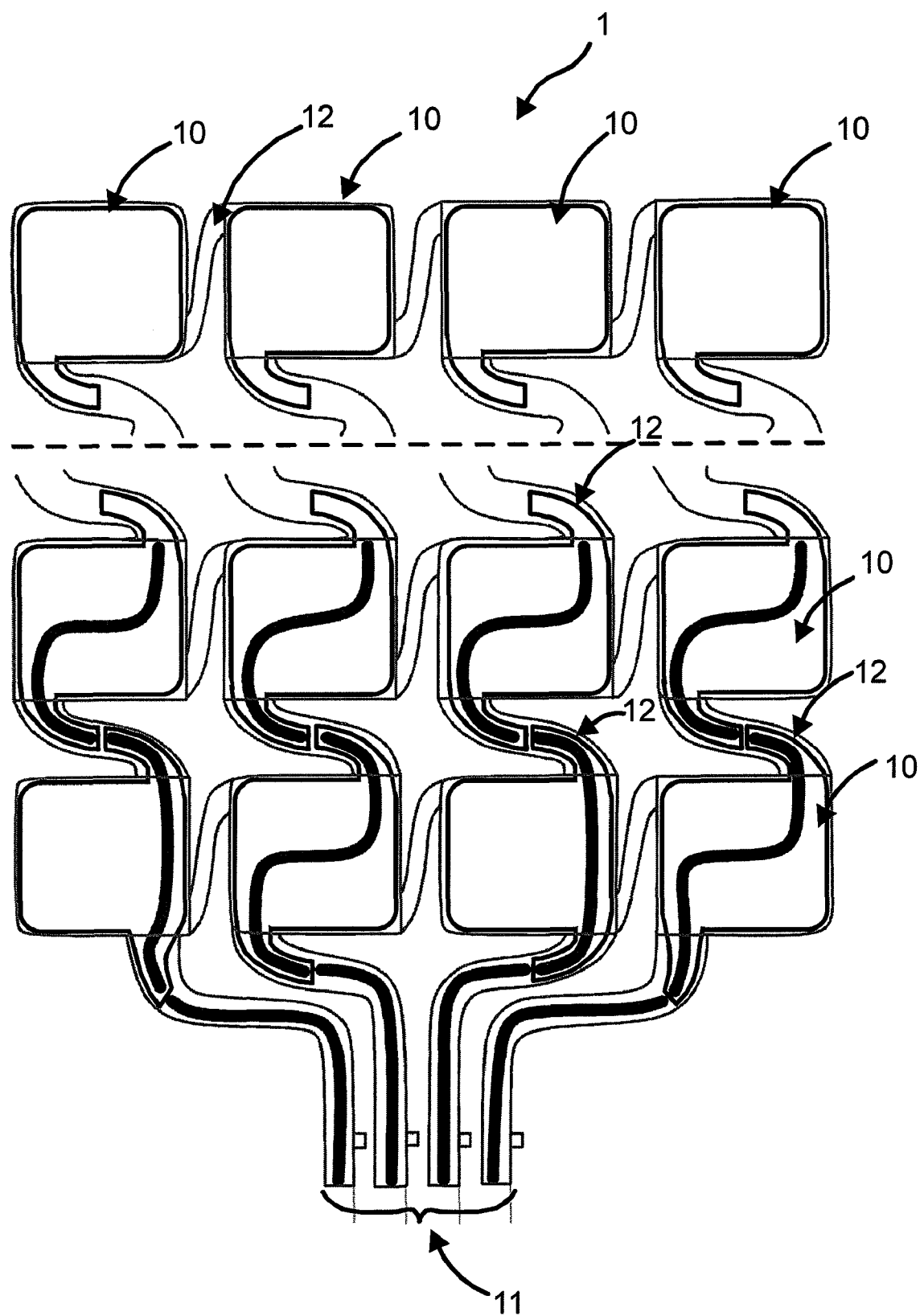

FIG. 1 shows a schema for a matrix type mattress foil sensor according to an embodiment of the invention, intended to be integrated into a bed mattress. The multichannel pressure sensing sensor in the form of a sheet comprises electrodes 10, which collect BCG signal data. The collected signal data is transferred to a terminal device via signal channels 11 for analyzing and processing. The electrodes 10 are connected to each other with narrow foil stripes 12 having a curved shape. The electrodes 10 cover approximately 50% of the total area of the multichannel pressure sensing sensor. When integrated into a bed mattress, the effective covering area increases as the pressing forces are spatially distributed in a soft tissue. For a point-like pressing force located between the electrodes 10, the soft tissue distributes part of the force to the neighboring electrodes.

Figure 2:
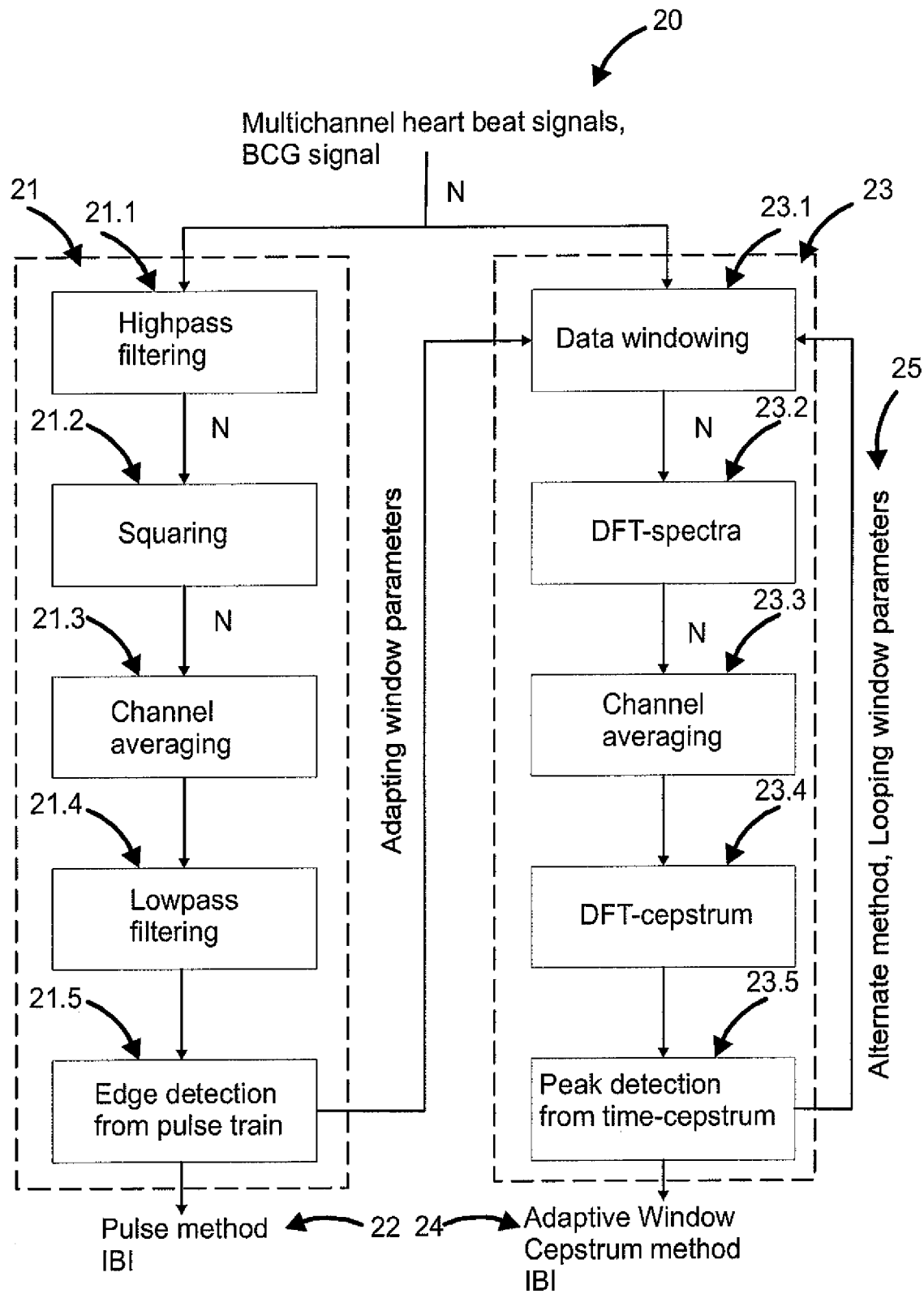
FIG. 2 shows a flowchart representation of the method according to a preferred embodiment of the invention.

FIG. 2 shows a flowchart representation of a preferred embodiment of the method for the heart beat extraction from the BCG signal 20, where multichannel signal path is shown with index N. The most common method for the heart beat extraction from the BCG signal uses signal filtering to generate a BCG pulse train method, titled as pulse method 21. The pulse method 21 uses high pass filtering of the signal in the first step 21.1 to generate a BCG pulse train. In the second step 21.2 the signal of each high pass filtered BCG signal channel is squared, and in the next step 21.3 these squared values between all channels are averaged and in the next step 21.4 the result is low pass filtered, and finally in the last step 21.5 the beginning of each heart beat in the generated pulse train signal is tracked.

The better accuracy of heart IBI is achieved by applying the DFT based deconvolution method called Adaptive Window Cepstrum method IBI 23 according to the present invention. The preferred selection of the DFT time window for a nonstationary BCG signal in the first step 23.1 includes exactly two consecutive heart beats. The heart beat interval varies strongly from beat to beat, and thus the Fourier transform should only be done for each pair of consecutive heart beats. The Adaptive Window Cepstrum method 23 selects the window length by using the pulse method 21 as the first estimator of the heart beats. The adaptive window length varies between one and several seconds depending on the actual heart rate. The spectrum for the BCG heart beat signal in the next step 23.2 is composed of the peaks at the harmonic frequencies of the fundamental heart beat frequency. The variance of the short time window DFT of the BCG signal is high. However, this variance can be decreased by averaging between multichannel BCG signals of the Adaptive Window Cepstrum method in the third step 23.3. The cepstrum $C_x$ is defined in the homomorphic deconvolution theory in the fourth step 23.4. It is the inverse Fourier transform of the logarithm of spectrum $S_x$:

$$S_x = F\{x\}$$

$$C_x = \text{real}(F^1[\log_e(|S_x|)])$$

The periodicity of the harmonic frequencies in the spectrum is shown in the last step 23.5 as a peak value in the cepstrum located at the corresponding heart IBI lag time value. The accuracy of this peak value is increased by averaging between multichannel signals, and thus it is possible to interpolate the location of peak maximum with better time resolution than the original data logging sampling rate. The sampling rate of 50 Hz corresponds with the time resolution of 20 milliseconds, but with the multichannel averaged cepstrum method and interpolation one can achieve even the time resolution of 5 milliseconds for each heart IBI value.

According to another embodiment of the invention, instead of using the adaptive window method 23, it is possible to use an alternative method, the alternative method 25, which uses a large set of constant parameter DFT window functions for different cepstra, estimates and updates each of these constantly by shifting in time. Computational efficiency of the alternative method 25 is not as good as with the Adaptive Window method 23, but the alternative method 25 is more straightforward to be implemented in the embedded system. The alternative method 25 is also more robust as it is not dependent on the possible detection inaccuracy of the individual heart beats with pulse method. The optimal selection criteria between the different heart IBI estimates with the alternative method 25 would firstly be based on the strength and sharpness of the found cepstra peaks, and secondly on how well they correspond to the neighboring IBI estimates. The latter relates to the fact that each IBI value should be equal to the time distance in between the corresponding heart beat locations. Additional information about the confidence value for the found heart IBI value is given from the average spectral power of the DFT window.

Figure 3:
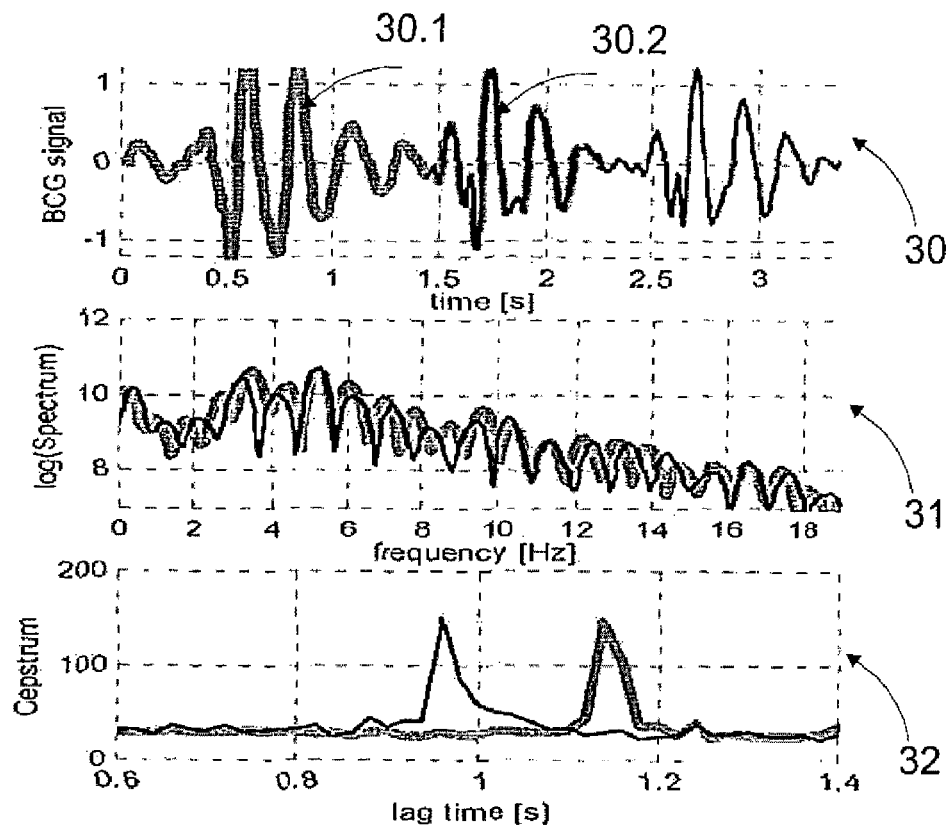
FIG. 3 shows a signal flow diagram of a signal measured and analyzed according to an embodiment of the invention.

FIG. 3 shows an example of a signal flow diagram of a measured signal, measured by a sensor according to one embodiment of the present invention, for a period of three heart beats including two heart IBI values to be estimated. The uppermost graph 30 shows one measurement channel of a sensor for measuring the BCG signal. The wide grey curve shows the DFT time window 30.1 for the first heart IBI period and the narrow black curve shows the following period 30.2. The middle graph 31 shows the logarithm of the spectrum and the lowermost graph 32 shows the cepstrum when both the first measuring result 30.1 and the following measuring result 30.2 are averaged between all measurement channels of the sensor. The first heart IBI result 30.1 with the grey curve is 1.14 seconds and the following heart IBI result 30.2 is 0.96 seconds. Variance of the DFT spectrum estimate is high, and averaging between the consequent time windows would impair the time resolution of the analysis and is not suitable for a nonstationary signal like BCG. It is possible to keep the original time resolution by averaging the DFT between sensor channels. The sampling rate of, for example, 50 Hz sets the resolution for the cepstrum lag time index into 20 milliseconds. It is preferred to use interpolation to find a more accurate location for the selected cepstrum maximum value.

Figure 4:
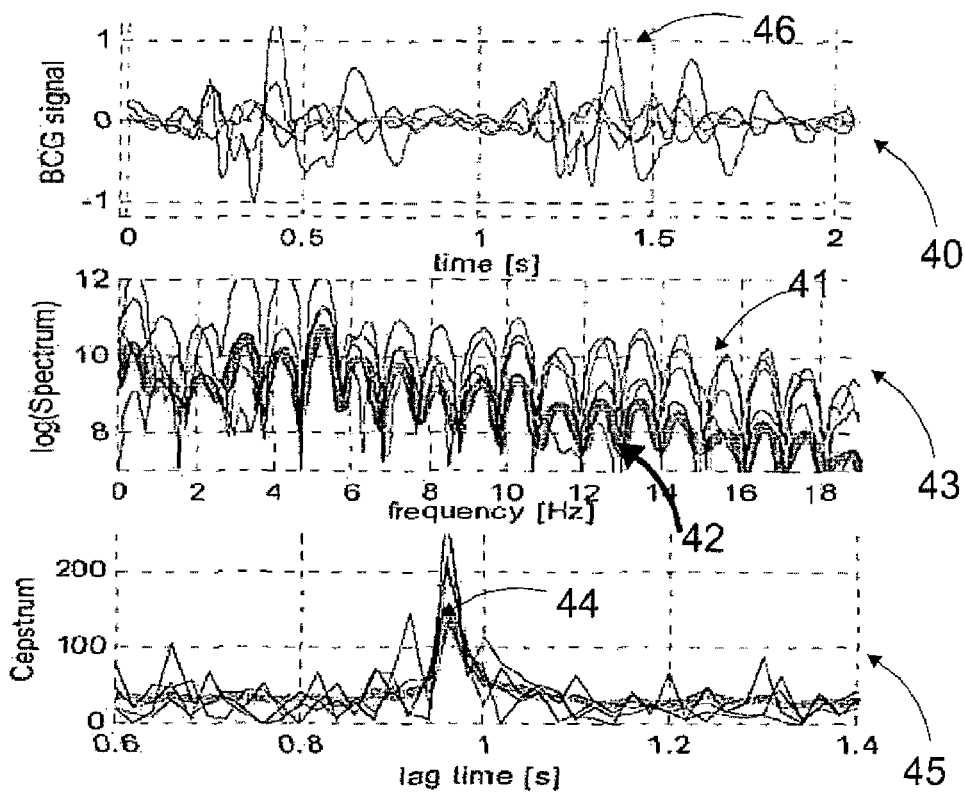
FIG. 4 shows a signal flow diagram of signals measured and analyzed according to an embodiment of the invention.

FIG. 4 shows a signal flow diagram of signals measured and analyzed according to one embodiment of the present invention. There are eight measured signals 46 in the uppermost graph 40, and individual DFT analyses 41 (shown with a black narrow curve) of those signals 46 and the averaged DFT 42 (shown with a wide grey curve) in the middle graph 43. The reduced variance is seen clearly in the averaged cepstrum 44 (with the grey color) at the lowermost graph 45. FIG. 4 shows a case, in which only eight measured signals 46 of 160 measured signals are shown, but the DFT averages 42, 44 are calculated for all 160 channels. An equally good accuracy for the channel averaged DFT could also be achieved with only 10 measurement channels by first combining the neighboring sensor electrodes with larger elements.

Figure 5:
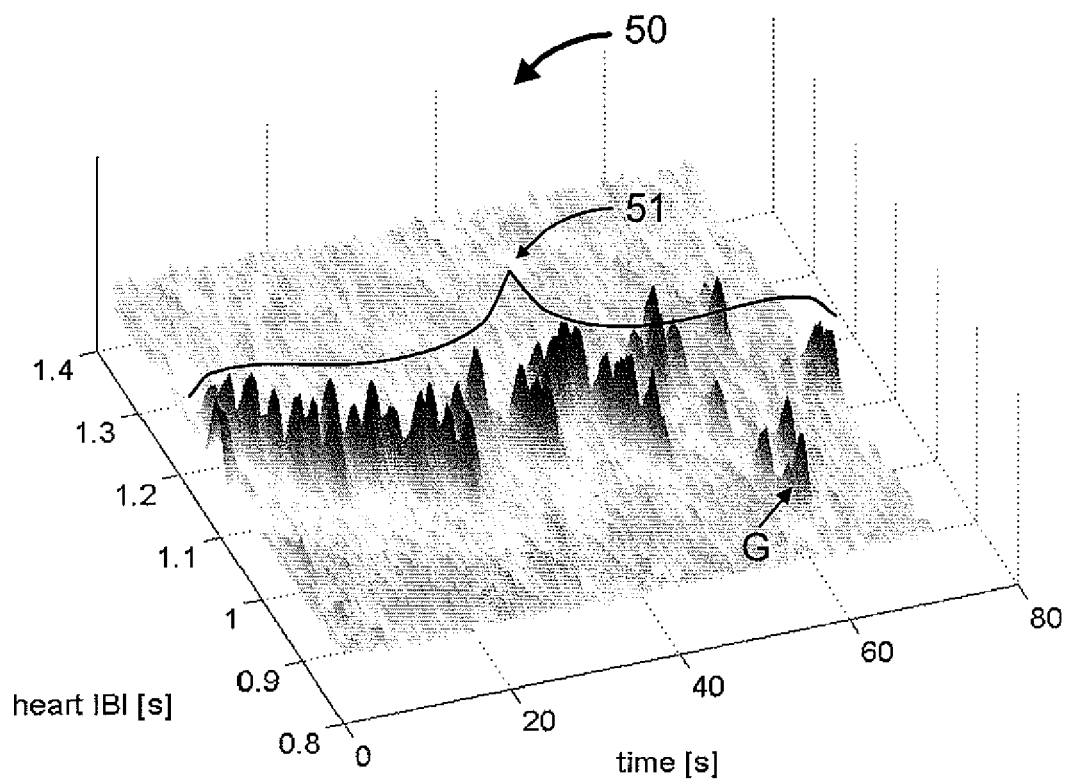
FIG. 5 shows a 3D-graph of the time-cepstrum result with an alternative method according to an embodiment of the invention.

FIG. 5 shows a time-cepstrum 3D graph 50 of the alternative method 25 during 70 seconds time period. Each pair of consequent heart beats shows a maximum 51 in the cepstrum, and the location of the maximum gives the corresponding heart IBI value in seconds, for example the point G shows the location of the maximum which corresponds with the lowest heart IBI value. Both the sharpness and the height of the peak 51 give a confidence value for the heart IBI value.

Figure 6:
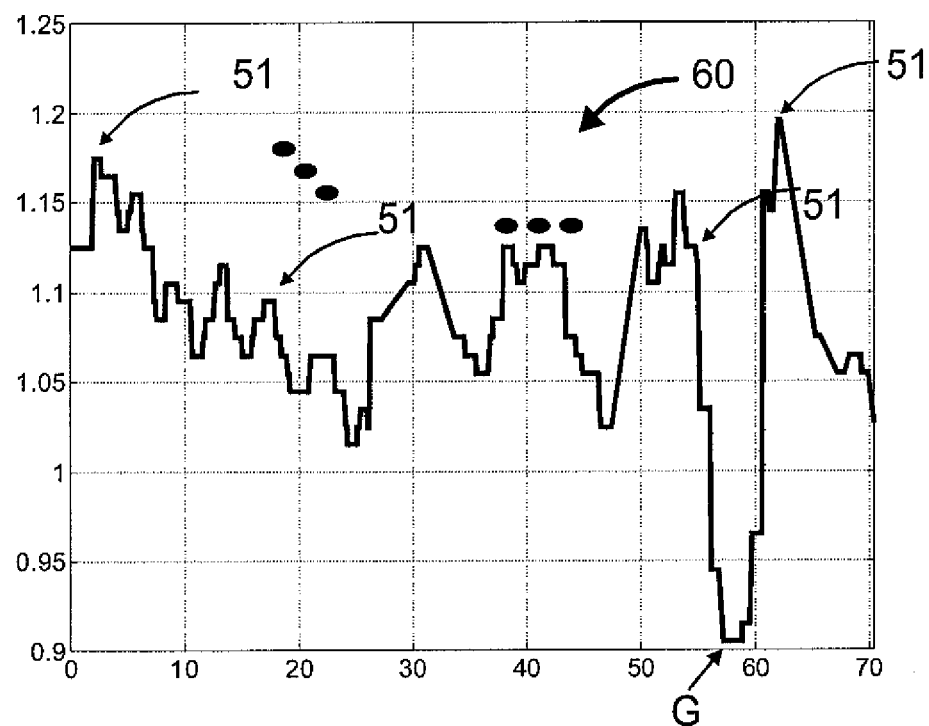
FIG. 6 shows the heart IBI results as the located maximum values from a time-cepstrum graph according to an embodiment of the invention.

FIG. 6 shows the final heart IBI result 60 of selected peak maximum 51 locations from the time-cepstrum graph 50 of FIG. 5 during 70 seconds. The point G shows the lowest heart IBI value.

Figure 7:
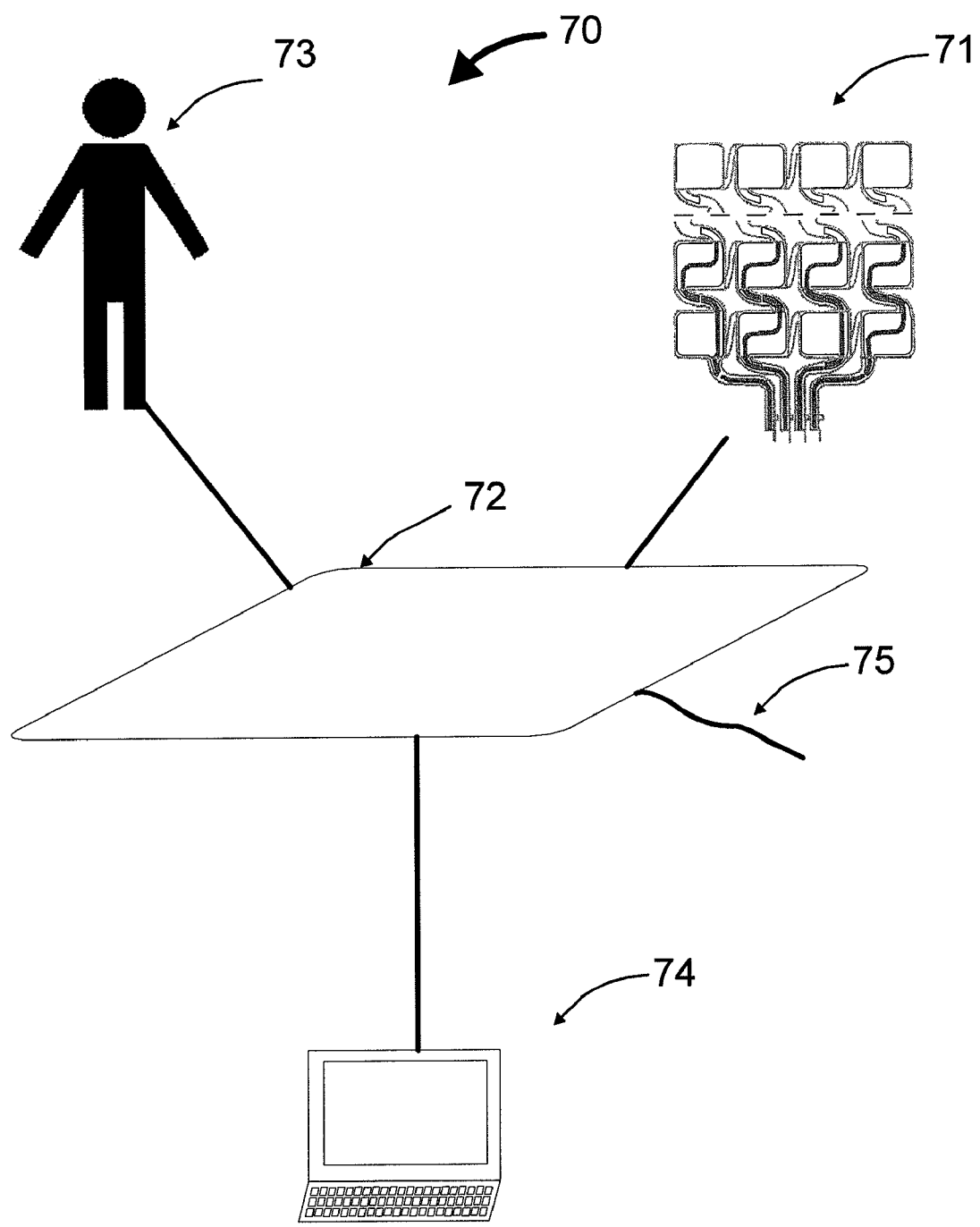
FIG. 7 shows a schema of measuring system components according to an embodiment of the invention.

FIG. 7 shows a schema of a measuring system 70 according to an embodiment of the invention. A multichannel pressure sensing foil sensor 71 is placed under a bed mattress 72. The sensor 71 and the bed mattress 72 are placed under the body of a patient 73. The sensor 71 comprises electrodes which measure multichannel BCG signal data. The measured BCG signal data is transferred to a terminal device 74 via signal channels 75 for analyzing, processing and storing. Heart IBI is extracted from this multichannel data with the cepstrum method in the terminal device 74.

The above-mentioned embodiments do not restrict the scope of the invention it is possible that the multichannel pressure sensing matrix foil intended to be integrated into a bed mattress is also used to measure other possible features, such as for example the posture and movements of the body, and respiration. The multichannel method for heart inter beat interval extraction can be applied for any multichannel measurements with sufficient integration. This could include e.g. photoplethysmogram measurements, microphones, pressure sensors on bed legs, capacitive sensors, or ECG sensors. In addition, also the shape, size and the number of channels in the sensor mattress can vary. In addition, this multichannel cepstrum method is suitable to be used for other BCG signals measured with another multichannel sensor than with a multichannel pressure sensing sensor, for example with a photoplethysmogram or with an apparatus based on microwave Doppler radar.

That which is claimed:

1. A monitoring apparatus comprising:
   a multichannel sensor for measuring a ballistocardiographic signal of a body, said multichannel sensor comprising at least two measurement channels;
   a selector for selecting a time window for a heart inter beat interval including two consecutive heart beats to be estimated;
   wherein the monitoring apparatus is configured for
   defining a spectrum for the ballistocardiographic signal for each selected time window;
   forming an average of the ballistocardiographic signal spectra of at least two measurement channels of the multichannel sensor;
   defining a cepstrum from the logarithm of the spectrum; and
   defining a heart inter beat interval on the basis of the cepstrum.

2. The monitoring apparatus according to claim 1, wherein the selection of the time window is based on at least one of ballistocardiographic (BCG) signal heart beat analysis, or looping for a multitude of pre-selected window lengths and shifting in time.

3. The monitoring apparatus according to claim 1, wherein the multichannel sensor is a multichannel pressure sensor.

4. The monitoring apparatus according to claim 3, wherein the multichannel pressure sensor is integrated into a bed mattress or to a seat.

5. The monitoring apparatus according to claim 3, wherein the multichannel pressure sensor is a matrix-type, row-type or column-type multi-electrode multichannel pressure sensor foil.

6. The monitoring apparatus according to the claim 3, wherein the multichannel pressure sensor is configured to be laid under a body.

7. A method for defining a heart inter beat interval comprising:
   measuring a ballistocardiographic signal of a body with a multichannel sensor comprising at least two measurement channels;
   selecting a time window for a heart inter beat interval including two consecutive heart beats to be estimated;
   defining a spectrum for the ballistocardiographic signal for each selected time window;
   averaging between signal spectra of at least two measurement channels of the multichannel sensor;
   defining a cepstrum from the logarithm of the spectrum; and
   defining a heart inter beat interval on the basis of the cepstrum.

8. A method according to claim 7, comprising selecting the time window on the basis of at least one of a ballistocardiographic (BCG) signal heart beat analysis, or looping for a multitude of pre-selected window lengths and shifting in time.

9. A method according to claim 7, comprising using a multichannel pressure sensor as said multichannel sensor.

10. A method according to claim 9, comprising using a matrix-type, a row-type or a column-type multi-electrode multichannel pressure sensor as said multichannel pressure sensor.

11. A method according to the claim 9, comprising laying the multichannel pressure sensor under a body.

12. A method according to claim 7, comprising using a multichannel pressure sensor integrated into a bed mattress or to a seat.

* * * * *